(12) United States Patent
Na et al.

(10) Patent No.: US 11,199,635 B2
(45) Date of Patent: Dec. 14, 2021

(54) DIGITAL X-RAY DETECTOR, DIGITAL X-RAY DETECTION DEVICE, AND MANUFACTURING METHOD THEREOF

(71) Applicant: LG DISPLAY CO., LTD., Seoul (KR)

(72) Inventors: Hyungil Na, Seoul (KR); Minseok Yun, Seoul (KR); Sangmo Byun, Goyang-si (KR)

(73) Assignee: LG DISPLAY CO., LTD., Seoul (KR)

( * ) Notice: Subject to any disclaimer, the term of this patent is extended or adjusted under 35 U.S.C. 154(b) by 0 days.

(21) Appl. No.: 16/886,127

(22) Filed: May 28, 2020

(65) Prior Publication Data
US 2020/0379132 A1 Dec. 3, 2020

(30) Foreign Application Priority Data
May 29, 2019 (KR) .................. 10-2019-0063434

(51) Int. Cl.
*H01L 27/146* (2006.01)
*G01T 1/20* (2006.01)
*G01N 23/04* (2018.01)
*A61B 6/00* (2006.01)

(52) U.S. Cl.
CPC ......... *G01T 1/20181* (2020.05); *G01N 23/04* (2013.01); *G01T 1/2002* (2013.01); *G01T 1/2018* (2013.01); *G01T 1/20188* (2020.05); *H01L 27/14609* (2013.01); *H01L 27/14612* (2013.01); *H01L 27/14663* (2013.01); *A61B 6/502* (2013.01); *H01L 27/14683* (2013.01)

(58) Field of Classification Search
CPC ............ G01T 1/20181; G01T 1/20188; G01T 1/2002; G01T 1/2018; A61B 6/502; G01N 23/04; H01L 27/14609; H01L 27/14612; H01L 27/14663; H01L 27/14683
See application file for complete search history.

(56) References Cited

U.S. PATENT DOCUMENTS

2019/0196030 A1* 6/2019 Yang .................. G01T 1/247

FOREIGN PATENT DOCUMENTS

KR 10-2015-0046624 A 4/2015

* cited by examiner

*Primary Examiner* — Mark R Gaworecki
(74) *Attorney, Agent, or Firm* — Birch, Stewart, Kolasch & Birch, LLP

(57) ABSTRACT

A digital X-ray detector, a digital X-ray detection device and a manufacturing method thereof are discussed. The digital X-ray detector includes a base substrate including an active region including a plurality of pixel regions, and a gate-in-panel (GIP) region as at least one side region to the active region; a PIN diode disposed in the active region and over the base substrate; a GIP driver disposed in the GIP region and over the base substrate; and a scintillator layer disposed over the PIN diode and the GIP driver so as to overlay the active region and at least a portion of the GIP region. In the present invention, damage of the driver due to X-ray is minimized while a bezel size is minimized.

17 Claims, 11 Drawing Sheets

| Examples | Vth:Before X-ray irradiation | Vth:After X-ray irradiation | ΔVth | Transistor curve |
|---|---|---|---|---|
| Comparative Example | 0.10 | −3.17 | −3.27 |  |
| Embodiment | 0.43 | −0.92 | −1.35 |  |

DIGITAL X-RAY DETECTOR, DIGITAL X-RAY DETECTION DEVICE, AND MANUFACTURING METHOD THEREOF

CROSS-REFERENCE TO RELATED APPLICATIONS

This application claims the priority to Korean Patent Application No. 10-2019-0063434 filed on May 29, 2019, in the Korean Intellectual Property Office, the disclosure of which is hereby incorporated by reference in its entirety into the present application.

BACKGROUND

1. Technical Field

The present disclosure relates to a digital X-ray detector including a GIP (gate-in-panel) driver in which damage of the driver due to X-ray is minimized while a bezel size is minimized, and a digital X-ray detection device including the same, and a manufacturing method thereof.

2. Description of the Related Art

Because X-ray is of a short wavelength, the X-ray can transmit an object easily. The transmittance of an X-ray depends on an inner density of the object. Therefore, an internal structure of the object can be observed by detecting the transmittance of the X-ray as transmitted through the object.

One of X-ray based inspection methods used in a medical field is a film printing scheme. However, in the film printing scheme, in order to check a result, an image is shot and then a film is printed. Thus, it can take a long time to check the result. Especially, in the film printing scheme, there can be some difficulties in storing and preserving the printed film.

Recently, a digital X-ray detector (DXD) using a thin-film transistor has been developed and widely used in the medical field.

Generally, the digital X-ray detector detects the transmittance of the X-ray transmitted through the object and displays an internal state of the object on a display based on the transmittance.

Therefore, the digital X-ray detector can display the internal structure of the object without using a separate film and a printed paper. Further, the DXD has an advantage that the result can be checked in real time immediately after X-ray photographing.

SUMMARY

In a digital X-ray detection device used in mammography, for example, in order to increase an imaging resolution of a portion of a body of a person to be imaged, it is required to minimize a bezel size of a digital X-ray detector that comes into contact with the body of the person to be imaged.

In general, a gate driver and a readout circuitry are attached, in the form of an integrated circuit (IC), to at least one bezel region of a digital X-ray detector.

Specifically, the gate driver and the readout circuitry can be implemented in the form of an integrated circuit using a chip-on-film (COF) scheme, and can be attached to one end of an array panel of a digital X-ray detector.

Due to the gate driver and the readout circuitry attached to one end of the array panel, a bezel region having a certain area or greater is needed. Thus, it is difficult to reduce a bezel size.

Accordingly, the present inventors have developed a digital X-ray detector in which a GIP (gate-in-panel) driver is applied to minimize the bezel size, and damage to the GIP driver due to X-ray is minimized, and have further developed a digital X-ray detection device including the digital X-ray detector and a manufacturing method of the digital X-ray detector.

One purpose of the present disclosure is to provide a digital X-ray detector including a GIP driver that can allow the bezel size to be minimized, a digital X-ray detection device including the same, and a manufacturing method thereof.

Further, another purpose of the present disclosure is to provide a digital X-ray detector in which damage to the GIP driver due to X-ray is minimized, a digital X-ray detection device including the same, and a manufacturing method thereof.

Moreover, still another purpose of the present disclosure is to provide a digital X-ray detector in which a size of a bezel of a contact portion in contact with a body of an imaging target, thereby improving an imaging resolution of the contact portion, and to provide a digital X-ray detection device including the same, and a manufacturing method thereof.

The purposes of the present disclosure are not limited to the above-mentioned purposes. Other purposes and advantages of the present disclosure, as not mentioned above, can be understood from the following descriptions and more clearly understood from the embodiments of the present disclosure. Further, it will be readily appreciated that the purposes and advantages of the present disclosure can be realized by features and combinations thereof as disclosed in the claims.

One embodiment of the present disclosure provides a digital X-ray detector having a GIP driver in which damage of the driver due to the X-ray is minimized while a bezel region is minimized, and a digital X-ray detection device including the same.

According to an embodiment, the digital X-ray detector can include a base substrate which includes an active region including a plurality of pixel regions, and a GIP region located in at least one side region of the active region; a PIN (P type semiconductor-Intrinsic type semiconductor-N type semiconductor) diode disposed in the active region and over the base substrate; a GIP driver disposed in the GIP region and over the base substrate; and a scintillator layer disposed over the PIN diode and the GIP driver so as to overlay the active region and at least a portion of the GIP region.

In this example, the GIP driver can include a transistor region and a signal-line region. The transistor region can be closer to the active region than the signal-line region is. The scintillator layer can overlay up to the transistor region.

Further, the digital X-ray detection device can include the digital X-ray detector as described above, a support for supporting the digital X-ray detector, and an X-ray light source spaced apart from the digital X-ray detector at a predefined spacing for irradiating X-ray to the digital X-ray detector. In this connection, a side face of the digital X-ray detector contacts a body of an imaging target, wherein the side face has the GIP region.

One embodiment of the present disclosure provides a manufacturing method of a digital X-ray detector having a GIP driver in which damage of the driver due to the X-ray is minimized while a bezel region is minimized.

According to an embodiment, the method can include defining, over a base substrate, an active region including a plurality of pixel regions, and a GIP region located in at least one side region of the active region; forming a PIN diode disposed in the active region and over the base substrate, and forming a GIP driver disposed in the GIP region and over the base substrate, thereby to form an array panel; and forming a scintillator layer over the PIN diode and the GIP driver of the array panel so as to overlay the active region and at least a portion of the GIP region.

The present disclosure has following effects and advantages but is not limited thereto.

First, in accordance with the present disclosure, the bezel region can be minimized by forming the GIP driver as the gate driver over the array panel rather than separately attaching the gate driver in a form of a gate integrated circuit, to the array panel.

Second, in accordance with the present disclosure, at least a portion including the transistor region of the GIP driver including the transistor region and the signal-line region is overlaid with the scintillator layer. Thus, the damage of the GIP driver due to the X-ray can be minimized.

Third, in accordance with the present disclosure, the GIP driver is formed in a contact region that comes into contact with the body of the imaging target, and the sealing layer overlaying the scintillator layer does not cover a side face of the base substrate, and an end part of the sealing layer is formed on the signal-line region. Thus, the bezel region is minimized so that the imaging resolution of the contact portion can be improved.

In addition to the above effects and advantages, specific effects and advantages of the present disclosure are described below in conjunction with descriptions of specific details to implement the present disclosure.

DETAILED DESCRIPTION OF THE EMBODIMENTS

Figure 1:
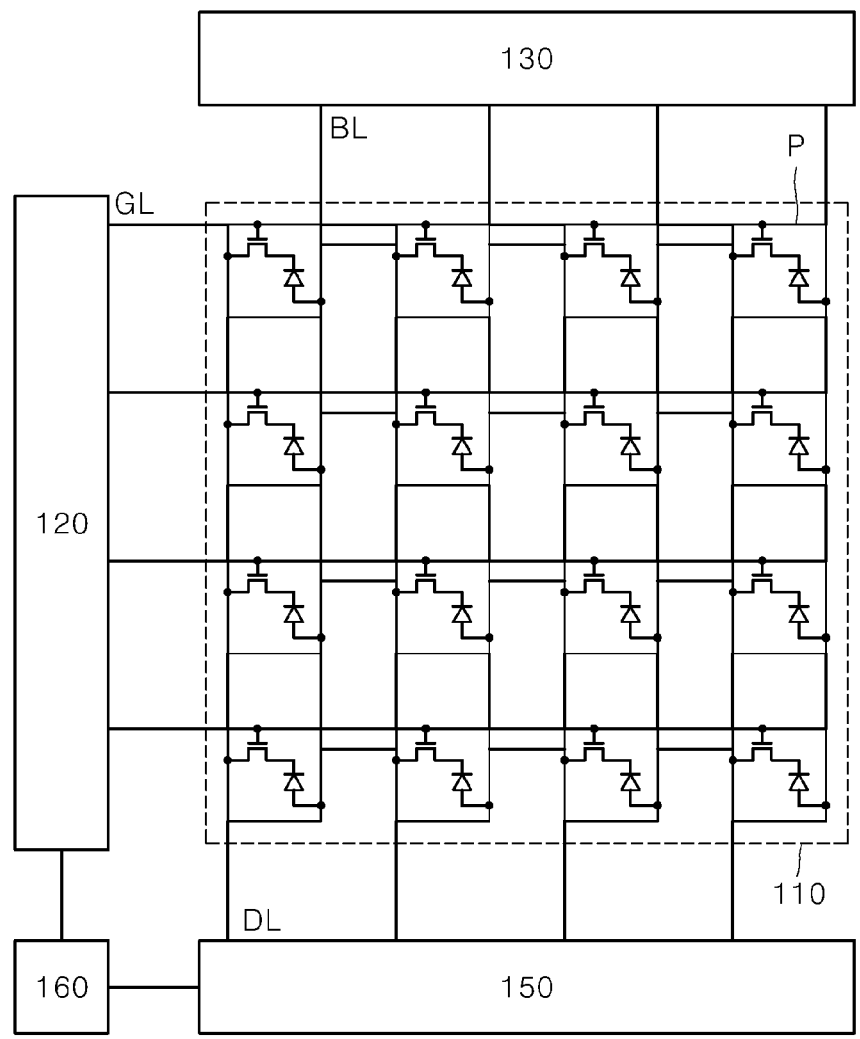
FIG. 1 is a block diagram to schematically illustrate a digital X-ray detector according to an embodiment of the present disclosure.
Figure 2:
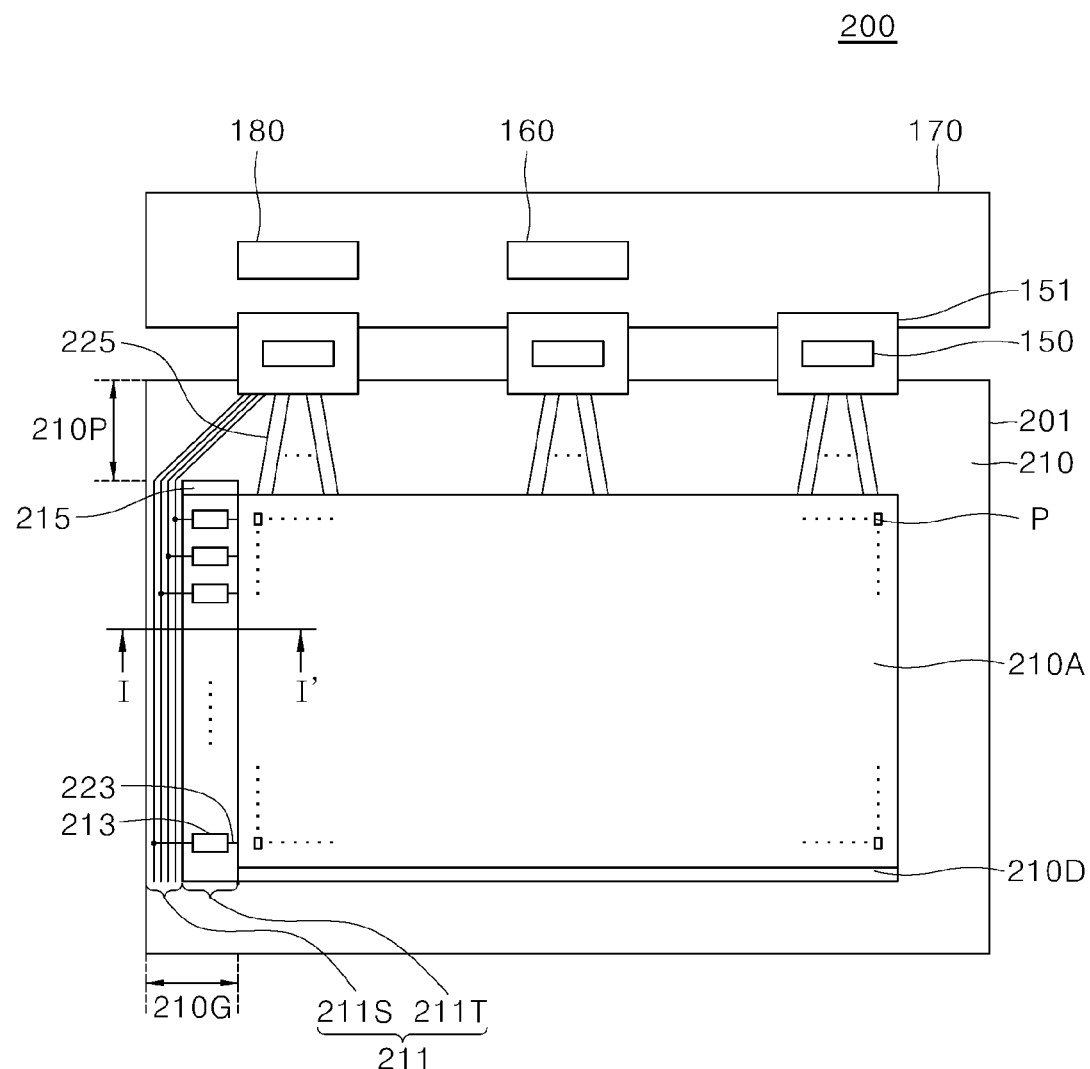
FIG. 2 is a schematic plan view of a digital X-ray detector according to an embodiment of the present disclosure.

For simplicity and clarity of illustration, elements in the figures are not necessarily drawn to scale. The same reference numbers in different figures denote the same or similar elements, and as such perform similar functionality. Furthermore, in the following detailed description of the present disclosure, numerous specific details are set forth in order to provide a thorough understanding of the present disclosure. However, it will be understood that the present disclosure can be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as can be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements can modify the entire list of elements and may not modify the individual elements of the list.

It will be understood that, although the terms "first", "second", "third", and so on can be used herein to describe various elements, components, regions, layers and/or sections, these elements, components, regions, layers and/or sections should not be limited by these terms and these terms may not define any order. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element can be disposed directly on or beneath the second element or can be disposed indirectly on or beneath the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers can be present. In addition, it will also be understood that when an element or layer is referred to as being "between" two elements or layers, it can be the only element or layer between the two elements or layers, or one or more intervening elements or layers can also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a digital X-ray detector according to some embodiments of the present disclosure, a digital X-ray detection device including the same, and a manufacturing method thereof will be described. All the components of the digital X-ray detector according to all embodiments of the present disclosure are operatively coupled and configured. All the components of the digital X-ray detection device according to all embodiments of the present disclosure are operatively coupled and configured.

FIG. 1 is a block diagram for schematically showing the digital X-ray detector.

Referring to FIG. 1, the digital X-ray detector can include a thin-film transistor array 110, a gate driver 120, a bias supply 130, a readout circuitry 150, and a timing controller 160.

The thin-film transistor array 110 includes a plurality of cell regions defined by a plurality of gate lines GL arranged in a first direction and by a plurality of data lines DL arranged in a second direction orthogonal to the first direction. The cell regions are arranged in a matrix form. Each cell region can include a pixel region in which photo-sensitive pixels P are formed. The thin-film transistor array 110 detects the X-ray emitted from an X-ray source and converts the detected X-ray into an electrical signal and outputs the electrical signal.

Each photo-sensitive pixel includes a PIN diode which converts light of a visible light region converted from the X-ray by a scintillator into an electronic signal and outputs the electronic signal, and a thin-film transistor TFT which transmits a detected signal output from the PIN diode to the readout circuitry 150. One end of the PIN diode can be connected to the thin-film transistor and the other end thereof can be connected to a bias line BL.

A gate electrode of the thin-film transistor can be connected to the gate line GL which carries a scan signal. Source/drain electrodes of the thin-film transistor can be respectively connected to the PIN diode and a data line DL which carries the detected signal output from the PIN diode. Each bias line BL can extend in a parallel manner to each data line DL.

The gate driver 120 can sequentially apply gate signals to thin-film transistors of photo-sensitive pixels through the gate lines GLs. The thin-film transistors of the photo-sensitive pixels can be turned on in response to the gate signals having a gate-on voltage level.

The gate driver 120 can be formed by directly stacking various devices such as transistors over the thin-film transistor array 110 in a gate-in-panel (GIP) form using a photolithography process.

The bias supply 130 can apply driving voltages to the photo-sensitive pixels through the bias lines BL. The bias supply 130 can selectively apply a reverse bias or a forward bias to the PIN diode.

The readout circuitry 150 can read out the detected signal transmitted from the thin-film transistor turned on in response to the gate signal of the gate driver 120. For example, the detected signal output from the PIN diode can be input to the readout circuitry 150 through the thin-film transistor and the data line DL.

The readout circuitry 150 can be formed in the form of an integrated circuit (IC) and can be directly mounted over the thin-film transistor array 110 or can be mounted over an external substrate such as a flexible printed circuit board (FPC) connected to the thin-film transistor array 110.

The readout circuitry 150 can have an offset readout period for reading out an offset image, and an X-ray readout period for reading out the detected signal output from each of the photo-sensitive pixels after an X-ray exposure.

The readout circuitry 150 can include a signal detector and a multiplexer. The signal detector includes a plurality of amplification circuits that correspond respectively to the data lines DL. Each amplification circuit can include an amplifier, a capacitor, and a reset element.

The timing controller 160 can control an operation of the gate driver 120 by supplying a control signal including a start signal STV and a clock signal CPV to the gate driver 120.

Further, the timing controller 160 can control an operation of the readout circuitry 150 by supplying a control signal including a readout control signal ROC and a readout clock signal CLK to the readout circuitry 150.

Hereinafter, a digital X-ray detector 200 according to one embodiment of the present disclosure will be described in detail with reference to FIG. 2 to FIG. 5.

The digital X-ray detector 200 according to one embodiment of the present disclosure includes a base substrate 210 in which an active region including a plurality of pixel regions P is defined.

The active region 210A can be formed as a rectangular region around a center of the base substrate 210. The base substrate 210 can be embodied as a glass substrate made of a glass material, but is not limited thereto. When a polyimide is used as a material for the base substrate 210, the base substrate 210 can act as a flexible substrate.

A region other than the active region 210A can be defined as non-active region. The non-active region can be positioned to surround a periphery of the active region 210A. The non-active region can include a bezel region.

In at least one side portion to the active region 210A, a gate-in-panel (GIP) region is defined. Thus, in the GIP region 210G and over the base substrate 210, a GIP driver 211 for applying a gate driving signal to the active region 210A can be formed.

The GIP driver 211 can be formed by directly stacking various devices such as transistor over the base substrate 210 in a gate-in-panel (GIP) form using a photolithography process.

The GIP driver 211 can include a transistor region 211T and a signal-line region 211S. The transistor region 211T can be closer to the active region 210A than the signal-line region 211S can be.

The transistor region 211T of the GIP driver 211 can include one or more GIP circuits 213.

The GIP circuit 213 can be connected to the active region 210A via a gate line 223, and can output a gate driving signal via the gate line 223.

Specifically, the GIP circuit 213 can act as a shift register circuit that sequentially outputs the gate signal, and can be connected to each of the gate lines 223 to output the gate signal.

The GIP circuit 213 can be composed of a plurality of transistors to act as a shift register.

Figure 4:
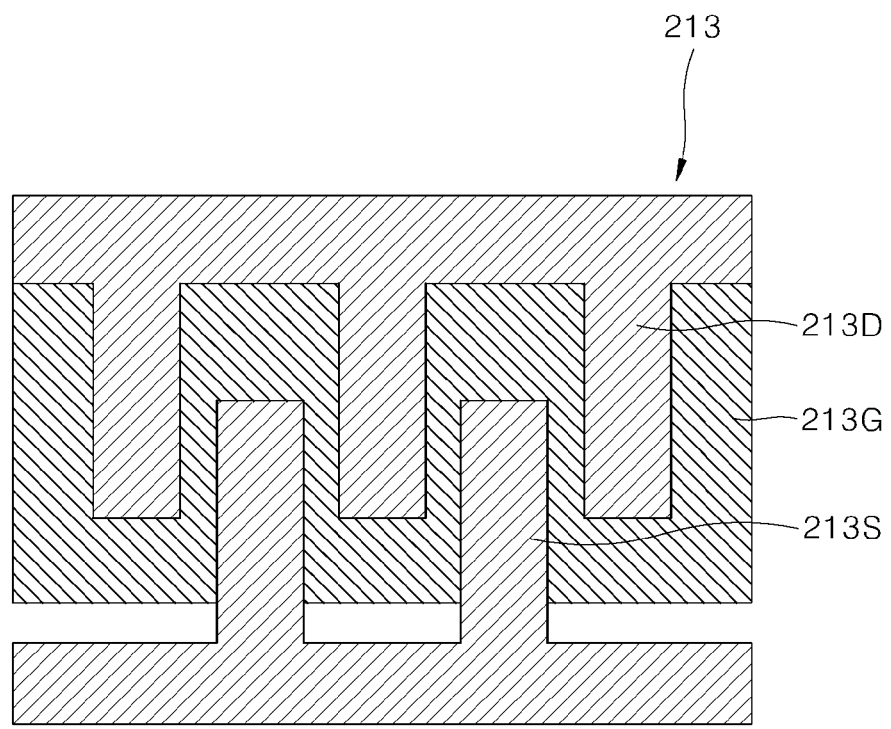
FIG. 4 is an enlarged view of a portion of a GIP circuit of a GIP driver according to an embodiment of the present disclosure.

For example, the GIP circuit 213 can be embodied as a multi-transistor type circuit in which GIP circuit drain electrodes 213D and GIP circuit source electrodes 213S are alternately arranged with each other, and a channel region is defined by underlying GIP circuit gate electrodes 213G, as shown in FIG. 4.

The GIP circuit 213 can receive a gate start signal Vst, multiple clock signals CLK of different phases, and a reset signal Rst.

The signal-line region 211S of the GIP driver 211 can supply the clock signal CLK received from the readout circuitry 150 to the GIP circuit 213 of the transistor region 211T. The supplied clock signal CLK can be output as a gate driving signal to be supplied to the gate lines 223 from the GIP circuit 213.

In one side portion of the active region 210A, a pad region 210P can be defined, so that a pad that receives a signal from an outside and transmits the signal to the active region 210A can be formed over the pad region 210P.

A readout integrated circuit of the readout circuitry 150 can be connected to the array panel 201 via the pad, and can output a readout signal via a data line 225.

Specifically, the readout circuitry 150 can be formed in the form of an integrated circuit and can be mounted over a flexible circuit film 151, and can be connected to the array panel 201 while being mounted over the flexible circuit film 151.

However, a form of the readout circuitry 150 is not limited thereto. The readout circuitry 150 can be directly mounted over the array panel 201 using a chip on glass (COG) scheme.

Further, in one example, the readout circuitry 150 can output the gate start signal Vst and the multiple clock signals CLK of different phases as a gate driving signal for driving the GIP circuit 213.

The gate driving signals CLK and Vst output from the readout circuitry 150 can be transmitted to the GIP circuit 213 via signal-lines of the signal-line region 211S in the GIP region 210G.

One end of the flexible circuit film 151 over which readout circuitry 150 is mounted can be connected to the array panel 201 and the other end thereof can be connected to a driving board 170. A power supply 180 and the timing controller 160 can be mounted over the driving board 170.

The power supply 180 can supply power to drive the driving board 170. The timing controller 160 can output a driving signal for driving the gate driver 120 and the readout circuitry 150.

An anti-static electricity circuit region 215 can be formed outside the active region 210A.

When static electricity is generated in the elements of active region 210A, and thus a high voltage or overcurrent having a magnitude equal or greater than a certain magnitude instantaneously flows therein, the anti-static electricity circuit region 215 can operate to electrically connect the elements of the active region 210A to a ground electrode to allow the static electricity to escape to a ground via the ground electrode.

In one embodiment of the present disclosure, the anti-static electricity circuit region 215 can be formed as one side region to the GIP region 210G, and can be formed, for example, between the GIP region 210G and the pad region 210P. However, the present disclosure is not limited thereto.

The anti-static electricity circuit region 215 can include an electrostatic discharge circuit (ESD) including a predetermined number of thin film transistors. In this case, a parasitic bipolar junction transistor can be used as the thin film transistor. However, the present disclosure is not limited thereto.

Further, a dummy region 210D can be formed in one side region to the active region 210A. The dummy region 210D has a structure similar to that of the pixel region in terms of elements, but does not actually operate as a pixel region.

Specifically, in a process of forming a pixel region, regions at an end of the pixel region where element characteristics can be deteriorated can be formed as the dummy region 210D. The dummy region 210D can be defined for a process margin.

In one embodiment of the present disclosure, the dummy region 210D can be formed in a lower region as one side region to the active region 210A. However, the present disclosure is not limited thereto.

In the active region 210A and over the base substrate 210, a plurality of thin film transistors 220 and PIN diodes 230 corresponding to the pixel regions respectively are formed.

Figure 5:
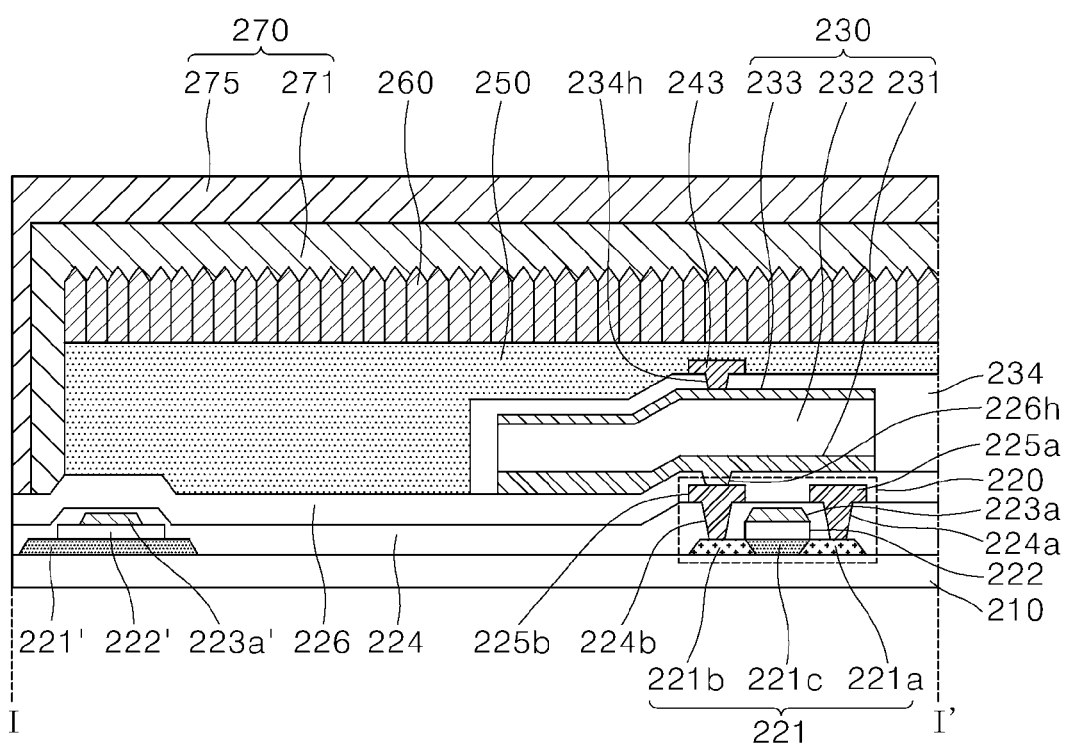
FIG. 5 is a cross-sectional side view of a digital X-ray detector according to an embodiment of the present disclosure.

FIG. 5 shows an arrangement structure of the thin film transistor 220 and the PIN diode 230 corresponding to one pixel region. Thus, the same arrangement structure can be applied to an adjacent pixel region. Further, the arrangement structure of the thin film transistor 220 and the PIN diode 230 according to FIG. 5 is only one embodiment, and the present disclosure is not limited thereto.

Over the base substrate 210, a plurality of cell regions are defined by a plurality of gate lines 223 and a plurality of data lines 225 intersecting with each other in an orthogonal manner Each pixel can correspond to each cell region so that a plurality of pixel regions are defined. A region corresponding to the gate line 223 and the data line 225 can be defined as a boundary region between pixel regions.

Over the base substrate 210, a thin film transistor 220 including a first electrode 225a, a second electrode 225b, a gate electrode 223a, and an active layer 221 is formed.

A buffer layer can be formed between the base substrate and the thin film transistor 220. In this case, the buffer layer can be made of an inorganic material of silicon oxide ($SiO_x$) or silicon nitride ($SiN_x$), and can be embodied as a multi-buffer layer composed of multiple sub-layers.

Over the base substrate 210, the active layer 221 is formed. The active layer 221 can be made of an oxide semiconductor material such as IGZO (Indium Gallium Zinc Oxide), but is not limited thereto. The active layer 221 can be made of low temperature polycrystalline silicon (LTPS) or amorphous silicon (a-Si).

The active layer 221 can include a channel region 221c and conductor regions sandwiching the channel region 221c therebetween. Specifically, the conductor regions can include a first conductor region 221a in direct contact with the first electrode 225a, and a second conductor region 221b in direct contact with the second electrode 225b.

The conductor regions of the active layer 221 can be formed by changing both ends of the active layer 221 to be conductive. Methods for changing both ends of the active layer 221 to be conductive can include various methods such as dry etching, hydrogen plasma treatment, and helium plasma treatment.

A gate electrode 223a is formed over the active layer 221. A gate insulating layer 222 is formed between the active layer 221 and the gate electrode 223a to insulate the active layer 221 and the gate electrode 223a from each other.

For example, the gate electrode 223a can be formed over the gate insulating layer 222 so as to correspond to the channel region 221c of the active layer 221. The gate electrode 223a can be made of one selected from a group consisting of molybdenum (Mo), aluminum (Al), chromium (Cr), gold (Au), titanium (Ti), nickel (Ni), copper (Cu), and alloy thereof and can be formed of a single layer or multiple layers.

The gate electrode 223a can extend from a gate line 223. A gate line 223 and the gate electrode 223a can be integrated with each other so that the gate electrode 223a is formed in the gate line 223. Accordingly, the gate line 223 and the gate electrode 223a can be formed in the same layer.

The gate insulating layer 222 made of an inorganic material can be formed to correspond to the gate electrode 223a, and can be formed to have the same as or larger area than an area of the gate electrode 223a for effective insulation.

The gate electrode 223a and the gate insulating layer 222 can be formed to correspond to a center of the active layer 221. Accordingly, a region of the active layer 221 as not overlaid by the gate electrode 223a and thus exposed, for example, both ends of the active layer 221 other than the channel region 221c can act as the first conductor region 221a and the second conductor region 221b.

An interlayer insulating layer 224 made of an inorganic material can be formed over the gate electrode 223a. The first electrode 225a and the second electrode 225b can be formed over the interlayer insulating layer 224.

The first electrode 225a and the second electrode 225b can be formed to respectively correspond to both sides of the active layer 221 while the gate electrode 223a is interposed therebetween. A first contact hole 224a and a second contact hole 224b can be formed in the interlayer insulating layer 224, respectively, in a region where at least a part of the active layer 221 and the first electrode 225a overlap each other and a region where at least a part of the active layer 221 and the second electrode 225b overlap each other.

Specifically, the first contact hole 224a can be formed to correspond to the first conductor region 221a of the active layer 221, while the second contact hole 224b can be formed to correspond to the second conductor region 221b. Accordingly, the first electrode 225a can be connected to the first conductor region 221a of the active layer 221 via the first contact hole 224a, while the second electrode 225b can be connected to the second conductor region 221b of the active layer 221 via the second contact hole 224b.

In this case, the first conductor region 221a can act as a drain region connected to the first electrode 225a as a drain electrode, while the second conductor region 221b can act as a source region connected to the second electrode 225b as a source electrode.

The first electrode 225a and the second electrode 225b can be extend from the data line 225, and can be formed in the same layer as that of the data line 225.

The data line 225 can be made of, but is not limited to, one selected from a group consisting of molybdenum (Mo), aluminum (Al), chromium (Cr), gold (Au), titanium (Ti), nickel (Ni), copper (Cu) and alloys thereof.

Over the thin film transistor 220, a first protective layer 226 can be formed to overlay an entirety of the base substrate 210. The first protective layer 226 can made of an inorganic material such as silicon oxide ($SiO_x$) or silicon nitride ($SiN_x$), but is not limited thereto. The first protective layer 226 can serve to protect the underlying thin film transistor 220, particularly, the active layer 221.

The PIN diode 230 is formed over the first protective layer 226 and is connected to the underlying thin film transistor 220.

The PIN diode 230 can include a lower electrode 231 connected to the thin film transistor 220, a PIN layer 232 over the lower electrode 231, and an upper electrode 233 over the PIN layer 232.

The lower electrode 231 can serve as a pixel electrode in the PIN diode 230. The lower electrode 231 can be made of an opaque metal such as molybdenum Mo or at least one of transparent oxides such as ITO (Indium Tin Oxide), IZO (Indium Zinc Oxide), and ZnO (Zinc Oxide), depending on characteristics of the PIN diode 230.

The lower electrode 231 can be connected to the second electrode 225b of the thin film transistor 220 via a third contact hole 226h as a contact hole in the first protective layer 226, so that the thin film transistor 220 can be connected to the PIN diode 230.

Over the lower electrode 231, the PIN layer 232 that converts visible light into an electrical signal can be formed. In this connection, a scintillator can convert the X-ray into the visible light. The PIN layer 232 can be formed by sequentially stacking a N (Negative) type semiconductor layer containing N type impurities therein, an I (Intrinsic) type semiconductor layer not containing impurities, and a P (Positive) type semiconductor layer including P type impurities therein.

The I-type semiconductor layer can be relatively thicker than each of the N-type semiconductor layer and the P-type semiconductor layer. The PIN layer 232 can be made of a material capable of converting the visible light into which the X-ray emitted from an X-ray source is converted into an electrical signal, for example, a-Se, $HgI_2$, CdTe, PbO, $PbI_2$, $BiI_3$, GaAs, and Ge.

The upper electrode 233 can be formed over the PIN layer 232. The upper electrode 233 can be made of at least one of transparent oxides such as ITO (Indium Tin Oxide), IZO (Indium Zinc Oxide), and ZnO (Zinc Oxide) and can improve a fill factor of the PIN diode 230.

A second protective layer 234 can be formed over the PIN diode 230. The second protective layer 234 can be made of an inorganic material such as silicon oxide (SiOx) or silicon nitride ($SiN_x$), but is not limited thereto. The second protective layer 234 can be formed to overlay up to a side face of the PIN diode 230 to protect the side face of the PIN diode 230 from moisture or other foreign substances.

A bias electrode 243 can be formed over the second protective layer 234 over the PIN diode 230. The bias electrode 243 can be connected to the upper electrode 233 of the PIN diode 230 via a fourth contact hole 234h as a contact hole in the second protective layer 234 and can apply a bias voltage to the PIN diode 230.

The bias electrode 243 can be branched from a bias line arranged in a parallel manner to the data line 225.

Over the bias electrode 243, a planarization layer 250 can be formed to overlay the PIN diode 230.

The planarization layer 250 can be formed to overlay at least a portion of the GIP region 210G including the active region 210A.

Specifically, an end of the planarization layer 250 may not be coincident with an end of the base substrate 210 and can be spaced from the end thereof. The planarization layer 250 can be formed to overlay, for example, up to the transistor region 211T of the GIP driver 211.

The planarization layer 250 can be made of an organic material such as PAC (photo acrylic).

The planarization layer 250 can have a thickness equal to or greater than a certain thickness to provide a planarized top face. Further, the planarization layer 250 serves as a growth base layer that enables a scintillator layer 260 formed over the PIN diode 230 to be well grown into a plurality of columnar crystals based on the planarization layer 250 made of the organic material.

Further, the planarization layer 250 can be advantageous in controlling leakage current. The planarization layer 250 has an advantage of being able to more easily control peeling of the scintillator layer 260 because the planarization layer 250 has excellent bonding strength with the scintillator layer 260 that can be made of an organic material.

The scintillator layer 260 is positioned over the PIN diode 230.

The scintillator layer 260 can be grown in a vertical direction to have a plurality of columnar crystal phases, so that a plurality of scintillator columnar crystals can be arranged in a side-by-side manner. The scintillator can be made of a material such as cesium iodide (CsI) or thallium iodide (TlI), but is not limited thereto.

The scintillator layer 260 can be formed over the PIN diode 230 and the GIP driver 211 to overlay the active region 210A and at least a portion of the GIP region 210G.

Figure 3:
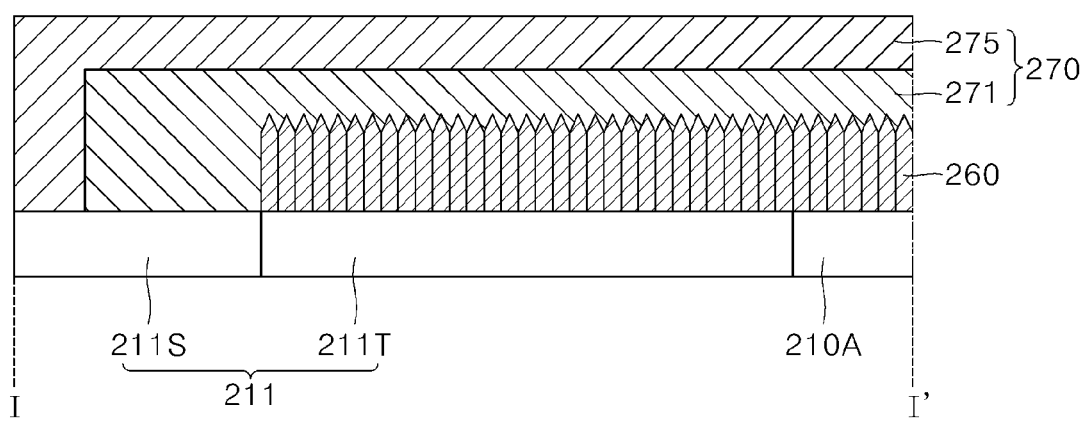
FIG. 3 is a schematic cross-sectional side view of a digital X-ray detector according to an embodiment of the present disclosure.

In this case, the scintillator layer 260 can be formed to overlay up to the transistor region 211T of the GIP driver 211 as shown in FIG. 3. The scintillator layer 260 can absorb the X-ray. For this reason, the scintillator layer 260 is formed to overlay the transistor region 211T of the GIP driver 211, thereby minimizing damage to the transistor region 211T due to exposure to the X-ray.

Over the scintillator layer 260, a sealing layer 270 can be formed to overlay the scintillator layer 260.

The sealing layer 270 can include a passivation layer 271 and a reflective layer 275.

The passivation layer 271 can play a role in minimizing penetration of moisture or other foreign substances into the scintillator layer 260 which is particularly susceptible to moisture. The passivation layer 271 can include or be made of an organic material such as parylene, but is not limited thereto.

The X-ray absorbed by the scintillator layer 260 is converted to visible light. Thus, the reflective layer 275 can serve to reflect the visible light not directed to the PIN diode 230 but directed outwardly toward the PIN diode 230.

The reflective layer 275 can include a light-scattering material such as $TiO_2$.

Specifically, the reflective layer 275 can be formed by applying a light-scattering reflective material including a light-scattering material such as $TiO_2$ and a binder resin.

However, the material of the reflective layer 275 is not limited thereto. An aluminum (Al) film having reflective properties can be used as the reflective layer.

The sealing layer 270 is formed so as not to cover a side face of the base substrate 210, thereby minimizing a bezel area of the digital X-ray detector 200.

Accordingly, an end part of the sealing layer 270 can be formed over the signal-line region 211S, or an end part of the sealing layer 270 can coincide with an end part of the base substrate 210.

Specifically, in accordance with the present disclosure, since the scintillator layer 260 overlays the transistor region 211T of the GIP circuit 213 but does not cover the signal-line region 211S thereof, the sealing layer 270 is in contact with a top face of the array panel 201 so that a sufficient sealing area can be secured.

Accordingly, sufficient sealing characteristics can be obtained even when the sealing layer 270 does not cover a side face of the base substrate 210. Further, a bezel area can be minimized.

Further, in accordance with the present disclosure, when an end part of the planarization layer 250 does not coincide with an end part of the base substrate 210, the sealing layer 270 can directly contact a large side face of the planarization layer 250, so that sealing characteristics can be further improved.

In particular, when a side face of the planarization layer 250 made of an organic material such as PAC and the passivation layer 271 made of an organic material such as parylene of the sealing layer 270 are in direct contact with each other, the sealing properties can be greatly improved due to a high bonding force between the organic material and the organic material.

The GIP circuit 213 can include a sequential stack of a GIP circuit active layer 221', a GIP circuit gate insulating layer 222', and a GIP circuit gate electrode 223a', and can be embodied as a plurality of multi-transistors.

The digital X-ray detector 200 according to the present disclosure operates as follows.

X-ray is irradiated to the digital X-ray detector 200. The scintillator layer 260 converts the X-ray into the visible light. The PIN layer 232 of the PIN diode 230 converts the light in the visible region into an electronic signal.

Specifically, when the light in the visible region is irradiated to the PIN layer 232, the I-type semiconductor layer is depleted by the P-type semiconductor layer and the N-type semiconductor layer, thereby generating an electric field therein. Then, holes and electrons generated by the light drift due to an electric field and are collected into the P-type semiconductor layer and the N-type semiconductor layer, respectively.

The PIN diode 230 converts the light in the visible region into the electrical signal and transmits the signal to the thin-film transistor 220. The electrical signal thus transmitted is displayed as an image signal via the data line 225 connected to the thin-film transistor 220.

Figure 6:
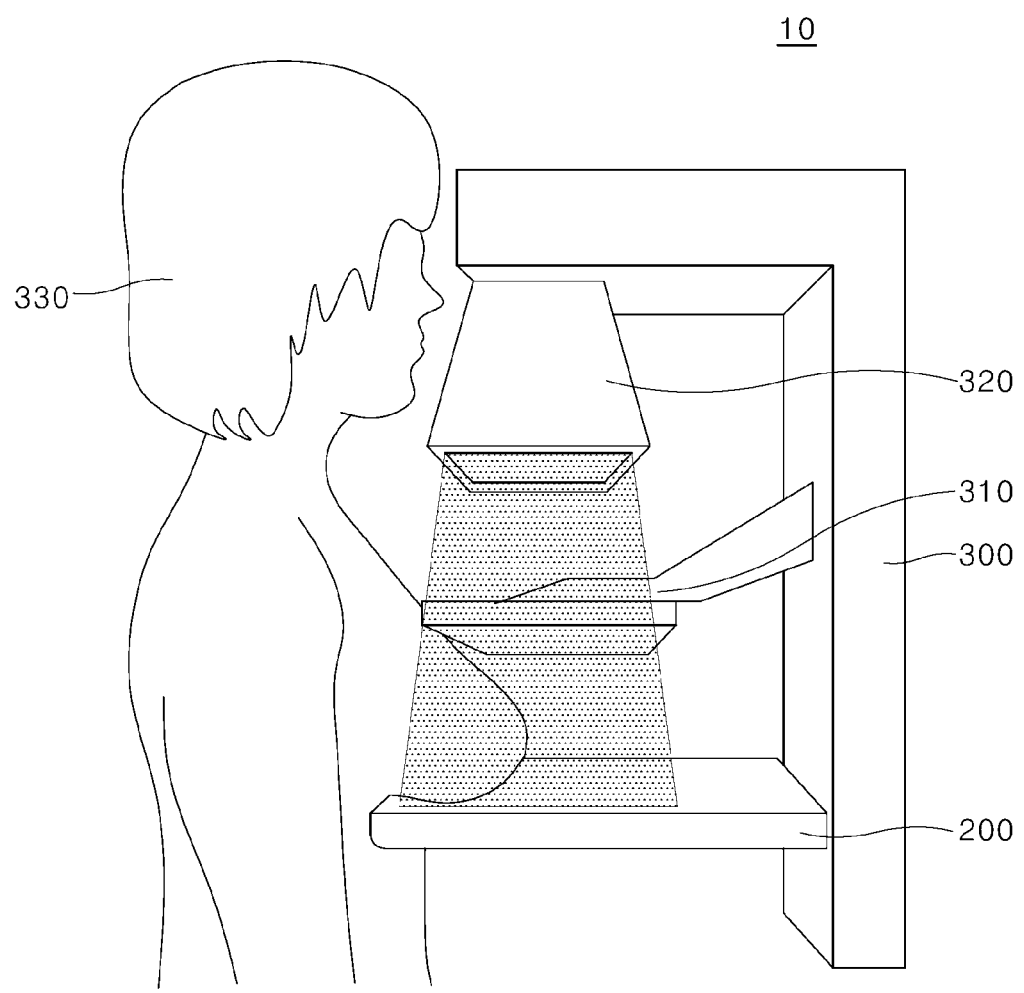
FIG. 6 shows a digital X-ray detection device according to an embodiment of the present disclosure.

As shown in FIG. 6, a digital X-ray detection device 10 according to one embodiment of the present disclosure includes the digital X-ray detector 200 according to one embodiment of the present disclosure, a support 300 for supporting the digital X-ray detector 200, and a light source 320 spaced, at a predetermined distance, from the digital X-ray detector 200 to irradiate the X-ray. Further, the digital X-ray detection device 10 can include a controller that controls an operation of each of the components.

FIG. 6 shows one example of the digital X-ray detection device 10 for mammography, but the digital X-ray detector or detection device can detect other parts of a human body or can be used for other purposes. In the example of FIG. 6, a body of an imaging target 330 can contact one side face of the digital X-ray detector 200.

In the digital X-ray detection device 10 for mammography, one side face of the digital X-ray detector 200 can be a chest wall that contacts a body of the imaging target 330.

Therefore, it is desirable to minimize a bezel region in one side face of the digital X-ray detector 200 corresponding to the chest wall so that a maximum imaging region can be secured.

Therefore, in accordance with the present disclosure, the digital X-ray detector 200 is positioned so that the side face of the digital X-ray detector 200 having the GIP driver 211 is a contact face that contacts the body of the imaging target 330, for example, the chest wall.

As illustrated above, the bezel region in the side face of the digital X-ray detector 200 having the GIP driver 211 is minimized, so that an effective imaging region in which the body of the imaging target 330 is imaged can be maximized.

A presser 310 that presses a portion of a body of the imaging target 330 to be imaged can be disposed between the digital X-ray detector 200 and the X-ray light source 320 and can be connected to the support 300.

For example, when the portion of the body of the imaging target 330 to be imaged has a predetermined thickness or greater, a significant amount of the X-ray is absorbed into an inside of the portion of the body. Thus, it can be difficult to obtain a captured image properly.

Therefore, if necessary, based on a physical condition of the imaging target 330 to be imaged, the presser 310 is moved in a vertical direction to press the portion of the body of the imaging target 330 to be imaged so that a clearer image can be obtained.

In this way, the digital X-ray detector 200 according to the present disclosure and the digital X-ray detection device 10 including the same can exhibit following advantageous effects.

First, in accordance with the present disclosure, the bezel region can be minimized by forming the GIP driver 211 as the gate driver 120 over the array panel 201 rather than separately attaching the gate driver 120 in the form of a gate integrated circuit, to the array panel 201.

When the gate driver 120 is mounted, in the form of a gate integrated circuit, over a separate substrate such as a flexible circuit film which then is separately attached to the array panel 201, the pad region 210P over which the pad is formed must be secured in the array panel 201.

For example, when the gate driver 120 is used as the gate integrated circuit and is connected to the array panel 201, it is difficult to minimize the bezel region while securing the separate pad region 210P.

However, in accordance with the present disclosure, since the GIP driver 211 acts as the gate driver 120, the separate pad region 210P is not required, so that the bezel region can be minimized.

Second, in accordance with the present disclosure, at least a portion including the transistor region 211T of the GIP driver 211 including the transistor region 211T and the signal-line region 211S is overlaid with the scintillator layer 260. Thus, the damage of the GIP driver 211 due to the X-ray can be minimized.

The GIP driver 211 includes the transistor region 211T including a plurality of GIP circuits 213 composed of multiple transistors. In this case, the transistors can be very vulnerable to the X-ray, and can be damaged when exposed directly to the X-ray.

Accordingly, in accordance with the present disclosure, the scintillator layer 260 can be formed over the transistor region 211T of the GIP driver 211. Thus, the damage to the transistor region 211T of the GIP driver 211 occurring when the transistor region 211T is directly exposed to the X-ray can be minimized.

Further, the scintillator layer 260 can be formed over the anti-static electricity circuitry 215 including an electrostatic discharge circuit ESD including a predetermined number of thin-film transistors. This can minimize the damage of the anti-static electricity circuitry occurring when the anti-static electricity circuitry is directly exposed to the X-ray.

Third, in accordance with the present disclosure, the GIP driver 211 is formed in a contact region that comes into contact with the body of the imaging target 330, and the sealing layer 270 overlaying the scintillator layer 260 does not cover a side face of the base substrate 210, and an end part of the sealing layer 270 is formed on the signal-line region 211S. Thus, the bezel region is minimized so that the imaging resolution of the contact portion can be improved.

According to the present disclosure, the scintillator layer 260 overlays the transistor region 211T of the GIP driver 211 but does not overlay the signal-line region 211S thereof. Thus, even when the sealing layer 270 does not cover the side face of the array panel 201, for example, the base substrate 210, a contact area between the sealing layer 270 and the array panel 201 can be secured to further minimize the bezel region.

Further, in accordance with the present disclosure, end part of the sealing layer 270 is formed on the signal-line region 211S. Thus, the sealing layer 270 can contact the signal-line region 211S of the base substrate 210, thereby to secure a sufficient sealing region. Thus, the sealing characteristics can be improved even when the bezel region is minimized.

For example, according to the present disclosure, the scintillator layer 260 does not overlay an entirety of the GIP region 210G, but overlays only the transistor region 211T, so that the signal-line region 211S can act as the sealing region. Thus, a separate sealing region is not required, so that the bezel region can be minimized.

In addition, according to the present disclosure, a cost for forming a separate gate integrated circuit can be reduced by forming the gate driver in the form of the GIP driver rather than in the form of the gate integrated circuit.

Further, when the gate driver is mounted, in the form of a gate integrated circuit, over a separate substrate such as a flexible circuit film which in turn is separately attached to the array panel, it can be difficult to implement a flexible digital X-ray detector. However, in accordance with the present disclosure, when the gate driver is implemented in the form of the GIP driver, it is easy to implement a flexible digital X-ray detector.

A manufacturing method of the digital X-ray detector 200 according to the embodiment of the present disclosure can include i) defining, over the base substrate 210, the active region 210A including a plurality of pixel regions, and a GIP region 210G located in at least one side region of the active region 210A, and forming the PIN diode in the active region 210A and over the base substrate 210, and forming the GIP driver 211 in the GIP region 210G and over the base substrate 210, thereby to form the array panel 201, and (ii) forming the scintillator layer 260 to overlay the active region 210A and at least a portion of the GIP region 210G of the array panel 201.

The manufacturing method of the digital X-ray detector 200 according to the embodiment of the present disclosure will be illustrated with reference to FIG. 7A to FIG. 7D based on a mask process.

A formation method of a pattern in each layer as exemplified below includes a technique performed by a person skilled in the art, for example, a photolithography process including deposition, photoresist coating, exposure, development, etching, and a photoresist strip, and thus, detailed descriptions thereof will be omitted.

For example, for the vapor deposition, sputtering is used for a metallic material, or plasma enhanced vapor deposition (PECVD) is used for a semiconductor or insulating film. Further, for the etching, dry etching and wet etching can be selectively used depending on a material. Techniques known to those skilled in the art are appropriately applied.

Figure 7A:
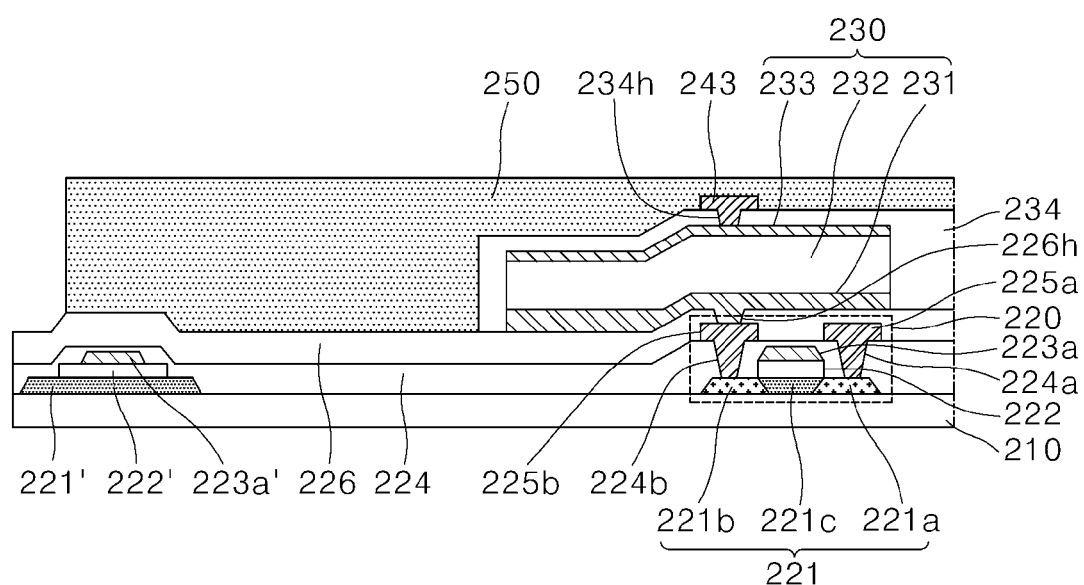
FIG. 7A to FIG. 7D show a process chart of a manufacturing method of a digital X-ray detector according to an embodiment of the present disclosure.

First, the array panel 201 is formed by forming the thin-film transistor 220 and the PIN diode 230 over the base substrate 210 where the active region 210A including a plurality of pixel regions is defined, as shown in FIG. 7A. A plurality of the thin-film transistors 220 and a plurality of the PIN diodes 230 can be formed to correspond to the pixel regions respectively.

The formation method and structure of each of the thin-film transistor 220 and the PIN diode 230 are not particularly limited and are known to by a person skilled in the art. Thus, detailed descriptions thereof can be omitted.

The GIP driver 211 can be formed over the base substrate 210 where the GIP region 210G is defined as at least one side region to the active region 210A.

The GIP driver 211 includes the transistor region 211T and the signal-line region 211S. The transistor region 211T can be formed to be disposed closer to the active region 210A than the signal-line region 211S can be.

The transistor region 211T includes at least one GIP circuit 213. The GIP circuit 213 can be formed by sequentially stacking the GIP circuit active layer 221', the GIP circuit gate insulating layer 222' and the GIP circuit gate electrode 223a'.

In this case, the GIP circuit active layer 221' is formed using the same process and material as those of the active layer 221 of the active region 210A. the GIP circuit gate insulating layer 222' is formed using the same process and material as those of the gate insulating layer 222 of the active region 210A. The GIP circuit gate electrode 223a' can be formed using the same process and material as those of the gate electrode 223a of the active region 210A.

Over the array panel 201, the planarization layer 250 is formed to overlay the PIN diode 230 and the GIP circuit 213.

The planarization layer 250 can be formed over the array panel 201 by spin coating the organic material PAC (photo acrylic). However, the present disclosure is not limited thereto.

An end part of the planarization layer 250 can be formed to be spaced, at a certain distance, from an end part of the base substrate 210 so that the former and the latter may not coincide with each other. In this case, the planarization layer 250 can be formed to overlay only the transistor region 211T of the GIP circuit 213.

Figure 7B:
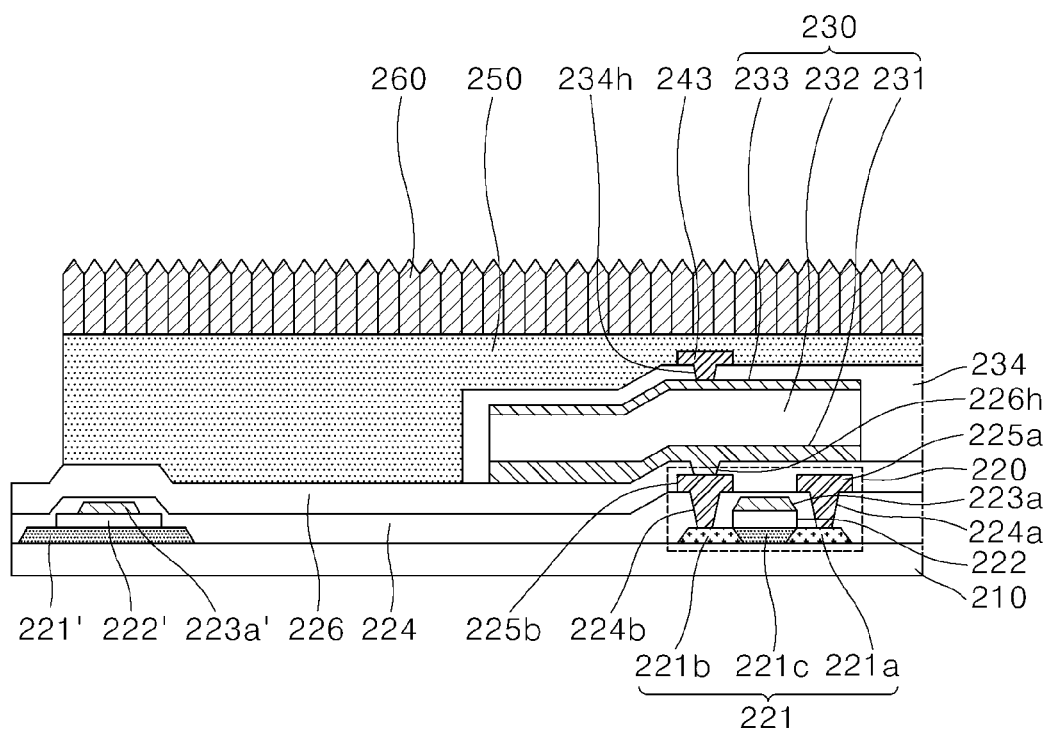

The scintillator layer 260 is formed over the planarization layer 250 as shown in FIG. 7B.

The scintillator layer 260 is grown in a vertical direction to have a plurality of columnar crystal phases via a deposition method while using the planarization layer 250 as a growth base layer. Thus, a plurality of scintillator columnar crystals can be arranged in a side by side manner.

For example, a seed for forming each scintillator columnar crystal is first formed over the planarization layer 250. Then, a crystal is grown on the seed in a vertical manner Thus, the scintillator layer 260 can be formed in a structure in which scintillator columnar crystals are arranged side by side and extend in the vertical direction.

The scintillator can be grown via crystallization in a temperature range of 150° C. to 230° C. using a halogen compound such as thallium (Tl) or sodium (Na)-doped cesium iodide (CsI). However, the present disclosure is not limited thereto.

The scintillator layer 260 can be formed to overlay the active region 210A and at least a portion of the GIP region 210G. Specifically, the scintillator layer 260 can be formed to overlay the active region 210A and up to the transistor region 211T of the GIP region 210G.

The scintillator layer 260 is formed to overlay the GIP circuit 213 of the transistor region 211T. Thus, the transistor region 211T can be prevented from being directly exposed to the X-ray, thereby minimizing the damage of the transistor region 211T occurring when being exposed to the X-ray.

For example, forming the scintillator layer 260 over the array panel 201 to overlay the transistor region 211T of the GIP region 210G, but to expose the signal-line region 211S to the outside can allow the contact area between the sealing layer 270 and the array panel 201 to be sufficiently secured.

Figure 7C:
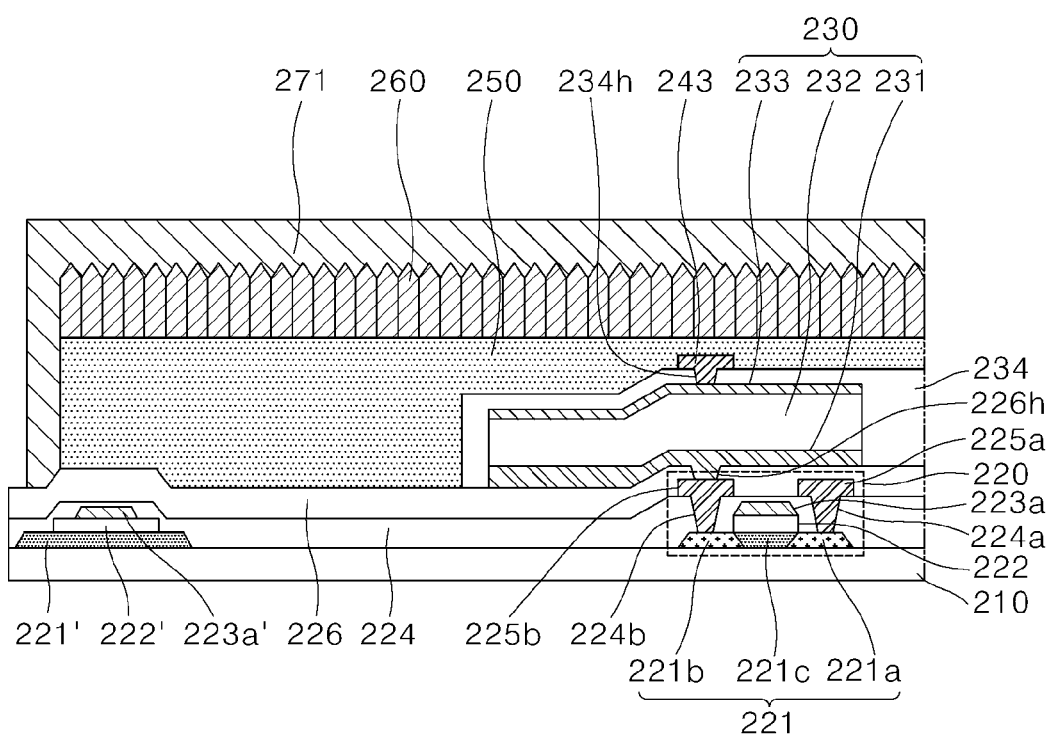
Figure 7D:
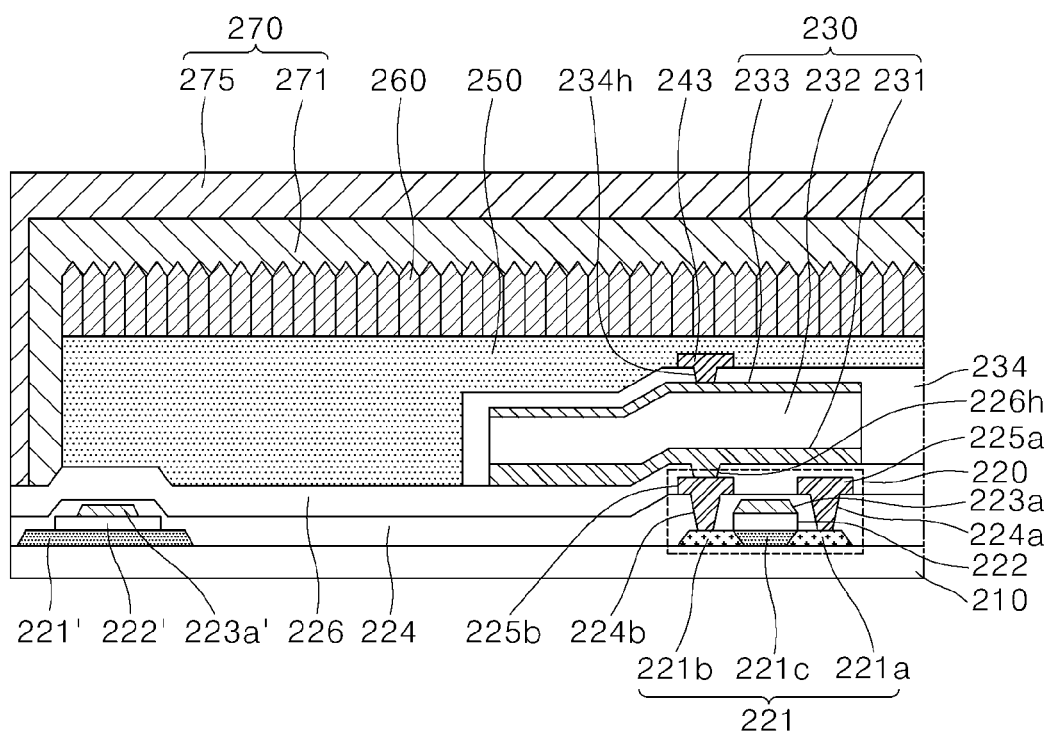

Next, as shown in FIG. 7C and FIG. 7D, the sealing layer 270 can be formed over the scintillator layer 260 to overlay the scintillator layer 260. Specifically, the sealing layer 270 can be formed by stacking the passivation layer 271 as shown in FIG. 7C and the reflective layer 275 as shown in FIG. 7D.

The material of the passivation layer 271 can include parylene. Specifically, after heating parylene powders to produce a reactive gas, the reactive gas reacts with the scintillator layer 260 and the base substrate 210 using a chemical vapor deposition to form the sealing layer 270.

The reflective layer 275 can include a light-scattering material such as $TiO_2$.

Specifically, the reflective layer 275 can be formed by applying a light-scattering reflective material including a light-scattering material such as $TiO_2$ and a binder resin.

However, the material for the reflective layer 275 is not limited thereto. Alternatively, an aluminum (Al) film having reflective properties can be embodied as the reflective layer.

The sealing layer 270 is formed so as not to cover the side face of the base substrate 210, so that the bezel region can be further minimized compared to a structure in which the sealing layer 270 covers the side face of the base substrate 210.

Specifically, an end part of the sealing layer 270 is formed on and contact the signal-line region 211S to sufficiently secure a contact area for sealing the sealing layer 270 and the base substrate 210, thereby improving the sealing characteristics and minimizing the bezel region.

A following experimental result demonstrated that the digital X-ray detector 200 having a structure according to an embodiment of the present disclosure has an improved effect compared to a conventional structure.

In Comparative Example, there is no scintillator layer 260 over the GIP circuit 213, whereas the scintillator layer 260 is disposed over the GIP circuit 213 in Embodiment of the present disclosure. Other configurations are the same therebetween.

In this experiment, X-ray having a tube voltage of 100 Kv and a tube current of 10 mA was irradiated to the digital X-ray detector away from the X-ray source by a distance of 50 cm for 79 minutes, and then change in a threshold voltage Vth was measured.

Figure 8:
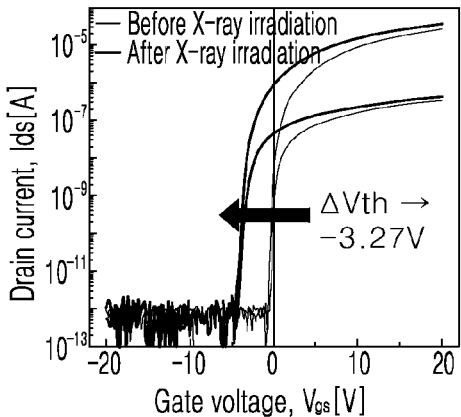
FIG. 8 shows comparison between threshold voltage ($V_{th}$) changes of a thin film transistor of a digital X-ray detector based on presence or absence of a shielding layer according to an embodiment of the present disclosure.
Figure 8:
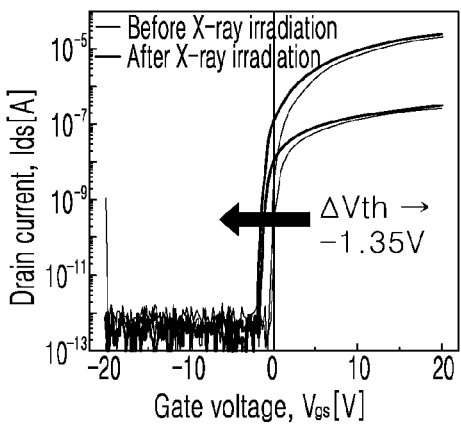

As shown in FIG. 8, in the Comparative Example, after the X-ray irradiation, a value of $\Delta V_{th}$ was −3.27. This confirms that a significantly large negative shift occurred after the X-ray irradiation.

On the other hand, in the Embodiment of the present disclosure as shown in FIG. 8, a value of $\Delta V_{th}$ is only −1.35 after X-ray irradiation. Thus, it can be seen that a very small negative shift occurred compared to the Comparative Example.

This confirms that when the scintillator layer 260 is formed over the GIP circuit 213 in accordance with the present disclosure, the amount of the negative shift is very small, thereby minimizing the deterioration of element characteristics.

The element is damaged by the X-ray as in the Comparative Example, and thus the value of the negative shift increases. In this case, the digital X-ray detector 200 needs to be set to an off state, but, the detector is actually set to an on state regardless of the user's settings. Thus, the thin-film transistor 220 is kept in an on state. This can lead to decrease in a lifespan of the digital X-ray detector 200.

As described above, the digital X-ray detector according to one or more embodiments of the present disclosure includes a base substrate including an active region including a plurality of pixel regions, and a GIP (Gate-in-panel) region located in at least one side region of the active region; a PIN (P type semiconductor-Intrinsic type semiconductor-N type semiconductor) diode disposed in the active region and over the base substrate; a GIP driver disposed in the GIP region and over the base substrate; and a scintillator layer disposed over the PIN diode and the GIP driver so as to overlay the active region and at least a portion of the GIP region.

In one implementation of the digital X-ray detector, the GIP driver includes a transistor region and a signal-line region, wherein the transistor region is closer to the active region than the signal-line region is, wherein the scintillator layer overlays up to the transistor region.

In one implementation of the digital X-ray detector, the transistor region includes at least one GIP circuit.

In one implementation of the digital X-ray detector, the detector further comprises a sealing layer disposed over the scintillator layer and overlaying the scintillator layer, wherein the sealing layer does not cover a side face of the base substrate.

In one implementation of the digital X-ray detector, an end part of the sealing layer is disposed on the signal-line region.

In one implementation of the digital X-ray detector, an end part of the sealing layer coincides with an end part of the base substrate.

In one implementation of the digital X-ray detector, the sealing layer includes a passivation layer and a reflective layer.

In one implementation of the digital X-ray detector, the passivation layer includes parylene, and the reflective layer includes a light-scattering material or is made of an aluminum (Al) film.

In one implementation of the digital X-ray detector, the detector further comprises a dummy region located in one side region of the active region; and an anti-static electricity circuit region located in one side region of the GIP region, wherein the scintillator layer is further located over the anti-static electricity circuit region.

As described above, the digital X-ray detection device according to the present disclosure includes the digital X-ray detector as defined above, a support for supporting the digital X-ray detector, and an X-ray light source spaced apart from the digital X-ray detector at a predefined spacing for irradiating X-ray to the digital X-ray detector.

In one implementation of the digital X-ray detection device, a side face of the digital X-ray detector contacts a body of an imaging target, wherein the side face has the GIP region.

In one implementation of the digital X-ray detection device, the digital X-ray detection device further comprises a presser disposed between the digital X-ray detector and the X-ray light source to press a body of an imaging target.

As described above, the method for manufacturing the digital X-ray detector according to one or more embodiments of the present disclosure includes defining, over a base substrate, an active region including a plurality of pixel regions, and a GIP (Gate-in-panel) region located in at least one side region of the active region; forming a PIN diode disposed in the active region and over the base substrate, and forming a GIP driver disposed in the GIP region and over the base substrate, thereby to form an array panel; and forming a scintillator layer over the PIN diode and the GIP driver of the array panel so as to overlay the active region and at least a portion of the GIP region.

In one implementation of the method, forming the GIP driver includes forming a transistor region and a signal-line region, wherein forming the transistor region and the signal-line region is performed so that the transistor region is closer to the active region than the signal-line region is, wherein forming the scintillator layer is performed so that the scintillator layer overlays up to the transistor region.

In one implementation of the method, forming the transistor region includes forming at least one GIP circuit.

In one implementation of the method, the method further comprises forming a sealing layer over the scintillator layer to overlay the scintillator layer, wherein forming the sealing layer is performed so that the sealing layer does not cover a side face of the base substrate.

In one implementation of the method, forming the sealing layer is performed so that an end part of the sealing layer is disposed on the signal-line region.

In one implementation of the method, forming the sealing layer is performed so that an end part of the sealing layer coincides with an end part of the base substrate.

In one implementation of the method, forming the sealing layer includes forming a passivation layer and a reflective layer.

The present disclosure is described with reference to the drawings and embodiments. However, the present disclosure is not limited to the embodiments and drawings disclosed herein. It will be apparent that various modifications can be made thereto by those skilled in the art within the scope of the present disclosure. Furthermore, although all the effects resulting from the configurations of the present disclosure have not been exhaustively listed in describing the effect resulting from the configurations of the present disclosure, the effects expected from the configurations of the present disclosure should be recognized.

What is claimed is:

1. A digital X-ray detector comprising:
   a base substrate including an active region including a plurality of pixel regions, and a GIP (gate-in-panel) region located in at least one side region of the active region;
   a PIN (P type semiconductor-Intrinsic type semiconductor-N type semiconductor) diode disposed in the active region and over the base substrate;
   a GIP driver disposed in the GIP region and over the base substrate; and
   a scintillator layer disposed over the PIN diode and the GIP driver so as to overlay the active region and at least a portion of the GIP region,
   wherein the GIP driver includes a transistor region and a signal-line region,
   wherein the transistor region is closer to the active region than the signal-line region is,
   wherein the scintillator layer overlays up to the transistor region, and
   wherein the transistor region includes at least one GIP circuit.

2. The digital X-ray detector of claim 1, wherein the digital X-ray detector further comprises a sealing layer disposed over the scintillator layer and overlaying the scintillator layer, and
   wherein the sealing layer does not cover a side face of the base substrate.

3. The digital X-ray detector of claim 2, wherein an end part of the sealing layer is disposed on the signal-line region.

4. The digital X-ray detector of claim 2, wherein an end part of the sealing layer coincides with an end part of the base substrate.

5. The digital X-ray detector of claim 2, wherein the sealing layer includes a passivation layer and a reflective layer, and
   wherein the passivation layer includes parylene, and the reflective layer includes a light-scattering material or is made of an aluminum (Al) film.

6. The digital X-ray detector of claim 1, wherein the digital X-ray detector further comprises:
a dummy region located in one side region of the active region; and
an anti-static electricity circuit region located in one side region of the GIP region, and
wherein the scintillator layer is further located over the anti-static electricity circuit region.

7. The digital X-ray detector of claim 6, wherein a pad region is defined in one side portion of the active region, and the anti-static electricity circuit region is disposed between the GIP region and the pad region.

8. The digital X-ray detector of claim 1, wherein a protective layer is disposed over the PIN diode, and the protective layer is disposed to overlay up to a side face of the PIN diode.

9. The digital X-ray detector of claim 8, wherein a planarization layer is disposed over the protective layer, and an end of the planarization layer is not coincident with an end of the base substrate.

10. The digital X-ray detector of claim 9, wherein the planarization layer is disposed to overlay up to the transistor region.

11. A digital X-ray detection device comprising:
a digital X-ray detector including:
a base substrate including an active region including a plurality of pixel regions, and a GIP (gate-in-panel) region located in at least one side region of the active region;
a PIN (P type semiconductor-Intrinsic type semiconductor-N type semiconductor) diode disposed in the active region and over the base substrate;
a GIP driver disposed in the GIP region and over the base substrate; and
a scintillator layer disposed over the PIN diode and the GIP driver so as to overlay the active region and at least a portion of the GIP region;
a support configured to support the digital X-ray detector; and
an X-ray light source spaced apart from the digital X-ray detector at a predefined spacing, and configured to irradiate X ray to the digital X-ray detector,
wherein a side face of the digital X-ray detector contacts a body of an imaging target, and the side face has the GIP region.

12. The digital X-ray detection device of claim 11, wherein the digital X-ray detection device further comprises a presser disposed between the digital X-ray detector and the X-ray light source to press the body of the imaging target.

13. A method for manufacturing a digital X-ray detector, the method comprising:
defining, over a base substrate, an active region including a plurality of pixel regions, and a GIP (gate-in-panel) region located in at least one side region of the active region;
forming a PIN (P type semiconductor-Intrinsic type semiconductor-N type semiconductor) diode disposed in the active region and over the base substrate, and forming a GIP driver disposed in the GIP region and over the base substrate, thereby to form an array panel; and
forming a scintillator layer over the PIN diode and the GIP driver of the array panel so as to overlay the active region and at least a portion of the GIP region,
wherein the forming the GIP driver includes forming a transistor region and a signal-line region,
wherein the forming the transistor region and the signal-line region is performed so that the transistor region is closer to the active region than the signal-line region is,
wherein the forming the scintillator layer is performed so that the scintillator layer overlays up to the transistor region, and
wherein the forming the transistor region includes forming at least one GIP circuit.

14. The method of claim 13, wherein the method further comprises forming a sealing layer over the scintillator layer to overlay the scintillator layer,
wherein the forming the sealing layer is performed so that the sealing layer does not cover a side face of the base substrate, and
wherein the forming the sealing layer includes forming a passivation layer and a reflective layer.

15. The method of claim 14, wherein the forming the sealing layer is performed so that an end part of the sealing layer is disposed on the signal-line region.

16. The method of claim 14, wherein the forming the sealing layer is performed so that an end part of the sealing layer coincides with an end part of the base substrate.

17. The method of claim 13, wherein the forming the scintillator layer includes growing scintillator of the scintillator layer via crystallization in a temperature range of approximately 150° C. to approximately 230° C. using a halogen compound.

* * * * *